United States Patent
Choi et al.

(10) Patent No.: US 10,149,833 B2
(45) Date of Patent: Dec. 11, 2018

(54) SMALL MOLECULE, INDIRUBIN-3-OXIME, FOR PREVENTION AND TREATMENT OF BONE DISEASE

(71) Applicant: Industry-Academic Cooperation Foundation, Yonsei University, Seoul (KR)

(72) Inventors: Kang-Yell Choi, Seoul (KR); Hyun-Yi Kim, Gyeonggi-do (KR); Sehee Choi, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 0 days.

(21) Appl. No.: 15/854,466

(22) Filed: Dec. 26, 2017

(65) Prior Publication Data
US 2018/0117007 A1  May 3, 2018

Related U.S. Application Data

(62) Division of application No. 14/328,169, filed on Jul. 10, 2014, now abandoned.

(30) Foreign Application Priority Data

Jul. 11, 2013 (KR) .................. 10-2013-0081464

(51) Int. Cl.
*A61K 31/404* (2006.01)
*A23L 33/10* (2016.01)
*A23L 33/105* (2016.01)
*A23L 2/52* (2006.01)

(52) U.S. Cl.
CPC .............. *A61K 31/404* (2013.01); *A23L 2/52* (2013.01); *A23L 33/10* (2016.08); *A23L 33/105* (2016.08); *A23V 2002/00* (2013.01)

(58) Field of Classification Search
USPC ......................................................... 514/414
See application file for complete search history.

(56) References Cited

U.S. PATENT DOCUMENTS

| 6,664,285 B1 | 12/2003 | Eisenbrand et al. |
| 2010/0015115 A1 | 1/2010 | Yie et al. |

OTHER PUBLICATIONS

U. Krause et al., "Pharmaceutical modulation of canonical Wnt signaling in multipotent stromal cells for improved therapy", Pnas (Mar. 2, 2010), 107(9), pgs. 4147-4152. nosteoinductive.
Kameswaran et. al., "Indirubin-3-monooxime induced cell cycle arrest and apoptosis in Hep-2 human laryngeal carcinoma cells," Biomedicine and Pharmacotherapy (2009) 63:146-154.

*Primary Examiner* — Marcos L Sznaidman
(74) *Attorney, Agent, or Firm* — Mintz Levin Cohn Ferris Glovsky and Popeo, P.C.; Kongsik Kim

(57) ABSTRACT

The present invention provides a composition comprising an indirubin derivative for stimulating longitudinal bone growth. Because the composition for stimulating longitudinal bone growth according to the present invention is shown to be effective in longitudinal bone growth, it may be used not only as a composition for stimulating longitudinal bone growth, but also as a pharmaceutical composition for treating or preventing short stature, microplasia, dwarfism, or precocious puberty.

4 Claims, 15 Drawing Sheets

SMALL MOLECULE, INDIRUBIN-3-OXIME, FOR PREVENTION AND TREATMENT OF BONE DISEASE

CROSS-REFERENCE TO RELATED APPLICATIONS

This application is a divisional application of U.S. application Ser. No. 14/328,169 filed on Jul. 10, 2014, which claims priority to Korean Application No. 10-2013-0081464 filed on Jul. 11, 2013, which applications are incorporated herein by reference.

TECHNICAL FIELD

The present invention relates to a small molecule, indirubin-3-oxime, for prevention and treatment of bone disease.

BACKGROUND ART

The increased awareness of the importance of normal growth, as well as an increased aesthetic interest, in infants and adolescents has led to an increased public interest in height growth. In the past, height growth was thought to depend on heredity. However, it is said that the proportion to which heredity is responsible for actual height growth is only 23%, and also, depending on the care during the period of growth, sufficient height growth can be achieved. Therefore, a great deal of money is being invested, estimated to be anywhere between 4-100 million dollars, to achieve height growth within the time period in which the growth plate is not closed. A public opinion survey shows that 33% of children in this growth period receive artificial care for height growth. Thus, there is also a growing number of therapeutic agents for growth, or hospitals that run growth clinics. However, most of the drugs that are currently in the market simply contain nutritional supplement components, and a question remains as to the proportion of therapeutic agents for growth that produce a real effect. Furthermore, virtually no drug has a target directly related to height growth. The Fair Trade Commission reports that even though the majority of therapeutic agents for growth that are distributed in the market are simply general food products or functional food products, they are labeled with terms such as "agent for height growth" or "(functional) food product for height growth." Developing a novel therapeutic agent for growth is therefore critical at this point, where proper therapeutic agents for growth are still lacking, in spite of consumption trends.

Meanwhile, height growth necessitates an increase in bone length, and endochondral ossification is associated with such an increase. Ossification can be largely classified as intramembraneous ossification and endochondral ossification. Intramembraneous ossification is a formation of bones in which calcium and phosphorus secreted from the osteoblasts are lumped together and gradually increase in size. It occurs in the periosteum on the outer surface of the bone edge, and relates to the increase in bone thickness. On the other hand, endochondral ossification is a formation of bones in which a cartilage model is formed and then an ossification center emerges at its center. This occurs in the epiphyseal plate and relates to the increase in longitudinal bone length. That is, the increase in bone thickness and that in bone length are caused by different ossification processes. Endochondral ossification is largely induced by endocrine factors and paracrine factors. Growth hormone injection, which is a drug that can stimulate the endocrine factors, is available to date. However, growth hormone injection is not suitable for a child with normal hormone secretion, and instead produces side effects when used, such as hypothyroidism and hyperpituitarism. Moreover, it is not easily accessible because of its high cost. In addition, a recent issue concerns precocious puberty causing early closure of the growth plate, thus shortening the period of growth. Since paracrine factors are involved in the actual closure of the growth plate, it can be said that targeting them is important for enhancing the effect of related drugs. Hence, the present inventors have investigated the Wnt/β-catenin signaling pathway, which is activated by Wnt, one of the paracrine factors that are involved in the increase in bone length, and found that the increase in longitudinal bone length is induced by indirubin-3'-oxime, one of the substances that activate β-catenin, which is a core signal transducer in this signaling pathway. The present inventors also sought to utilize the substance to induce height growth. Indirubin-3'-oxime was synthesized as a derivative of indirubin, a component found in the roots or leaves of indigo plants, used for the Chinese medicine, Danggui Longhui Wan. It is also known to be free of toxicity. The present inventors have found that indirubin-3'-oxime, in particular, activates the growth plate by stimulating chondrocytes, which are involved in height growth, in the growth plate. Unlike conventional therapeutic agents for growth, indirubin-3'-oxime regulates the signaling pathway based on specific targets involved in height growth, and is therefore effective in inducing height growth specifically. Furthermore, because indirubin, which is the source substance for indirubin-3'-oxime, is a low molecular weight compound that has already reached the second stage of clinical trial as a therapeutic agent for leukemia, its safety is more or less guaranteed. Moreover, the development cost for indirubin-3'-oxime is relatively low. Thus, the expected effect is very large for utilizing indirubin-3'-oxime as a therapeutic agent for height growth.

SUMMARY

Thus, drugs targeting β-catenin, which is one of paracrine factors involved in the increase in bone length, are required.

To achieve said purpose, the present invention provides in an embodiment a composition comprising an indirubin derivative for stimulating bone growth. Another embodiment provides a composition wherein the indirubin derivative is indirubin-3'-oxime. Another embodiment provides a composition wherein the bone growth is an increase in the length of the tibia. Another embodiment provides a composition wherein the bone growth is an increase in the activity of the growth plate.

In addition, an embodiment of the present invention provides a pharmaceutical composition comprising an indirubin derivative for treating or preventing bone growth disorders. Another embodiment provides a pharmaceutical composition wherein the indirubin derivative is indirubin-3'-oxime. Another embodiment provides a pharmaceutical composition wherein the bone growth disorder is short stature, microplasia, dwarfism, or precocious puberty.

Furthermore, an embodiment of the present invention provides a food composition comprising an indirubin derivative for improving bone growth. Another embodiment provides a food composition wherein the indirubin derivative is indirubin-3'-oxime. Another embodiment provides a food composition wherein the longitudinal bone growth is an increase in the length of the tibia. Another embodiment provides a food composition wherein the bone growth is an increase in the activity of the growth plate.

Moreover, an embodiment of the present invention provides a functional beverage composition comprising an indirubin derivative for improving longitudinal bone growth. Another embodiment provides a functional beverage composition wherein the indirubin derivative is indirubin-3'-oxime. Another embodiment provides a functional beverage composition wherein the longitudinal bone growth is an increase in the length of the tibia. Another embodiment provides a functional beverage composition wherein the longitudinal bone growth is an increase in the activity of the growth plate.

Indirubin is an indigoid compound which is very similar in structure as indigo and which has a red color. It is generally produced in small amounts as a byproduct during a production of the blue dye indigo, using natural indigo (*Polygonum tinctorium*), woad (*Isatis tinctoria*), etc. Danggui Longhui Wan, a prescription in traditional Chinese medicine, is comprised of 11 types of medicines that have been used to treat chronic leukemia. Among these, indirubin has been found to be an effective drug. Moreover, as a cell cycle inhibitor, it was recently reported to be a drug of great value for medical applications, including a therapeutic agent for chronic leukemia, neurodegenerative diseases such as Alzheimer's, and the like (*Bri. J. Haemato.*, 130:681-690, 2005; *Nature Cell Biol.*, 1:60-67, 1999). Indirubin can form many derivatives around its parent structure, including indirubin oxime derivatives, indirubin hydrazone derivatives, indirubin N-acetyl derivatives, indirubin amine derivatives, etc.

The Wnt/β-catenin signaling pathway is a signaling pathway that plays a key role in the development, growth, and maintenance of homeostasis in vertebrates. It is known that the presence of an abnormality in the Wnt/β-catenin signaling pathway can cause an abnormality in bone formation (Liu et al., *Cell signal.*, 2008). The activation of the Wnt/β-catenin signaling pathway begins with the binding of Wnt, a ligand; Frizzled (Fz), a receptor; and lipoprotein receptor-related proteins 5 and 6 (LRP 5/6), a co-receptor. In the absence of Wnt signals, β-catenin, which is a core signal transducer in said signaling pathway, forms a complex with substances that interfere with signal transduction, such as Axin, GSK3, Apc, etc., and said complex is thus degraded by ubiquitination. Once the activation of signal transduction is initiated by Wnt stimuli, these complexes are disassembled, and 3-catenin is stabilized and accumulated in the cytoplasm, after which it is translocated into the nucleus to facilitate the expression of target genes through interaction with transcription factors, such as Tcf, Lef, or the like. Here, β-catenin is the most important molecule in the Wnt/β-catenin signaling pathway, and is well known to be involved in the increase in bone length. In the present invention, substances that increase the amount of β-catenin were tested for their ability to stimulate the increase in bone length, and among these, indirubin-3'-oxime was found to have such an effect. Indirubin-3'-oxime, a GSK3 inhibitor, blocks the decomposition of β-catenin and increases β-catenin translocation into the nucleus, thus increasing the expression of genes necessary for the proliferation and differentiation of chondrocytes. The present inventors confirmed through ex vivo and in vivo systems that indirubin-3'-oxime increases the length of the tibia. Because indirubin-3'-oxime increases height by targeting a specific mechanism, it is expected to be useful as a new therapeutic agent for height growth.

The pharmaceutical composition according to the present invention may further comprise suitable carriers, excipients, and diluents that are typically used for the preparation of pharmaceutical compositions.

The pharmaceutical composition according to the present invention may be formulated and used in the form of oral formulations, including powders, granules, tablets, capsules, suspensions, emulsions, syrups, aerosols, etc., external preparations, suppositories, or injectable solutions. Carriers, excipients, and diluents that may be comprised in a composition comprising an extract include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. For formulation, the composition is prepared using common diluents or excipients, such as fillers, extending agents, binding agents, wetting agents, disintegrating agents, and surfactants. Solid formulations for oral administration include tablets, pills, powders, granules, capsules, etc. Such solid formulations are prepared by mixing at least one excipient, e.g., starch, calcium carbonate, sucrose or lactose, gelatin, etc., with said extract. Besides the simple excipients, lubricants, such as magnesium stearate and talc, are also used. Liquid formulations for oral administration include suspensions, emulsions, syrups, etc. In addition to liquid paraffin, which is a commonly used simple diluent, a variety of excipients may be included, e.g., wetting agents, sweeteners, aromatics, preservatives, etc. Formulations for parenteral administration include sterilized solutions, non-aqueous solvents, suspensions, emulsions, lyophilized formulations, and suppositories. For non-aqueous solvents and suspensions, vegetable oils, such as propylene glycol, polyethylene glycol, and olive oil, injectable esters, such as ethyl oleate, or the like may be used. For suppository bases, Witepsol, Macrogol, Tween 61, cacao butter, laurinum, glycerogelatin, or the like may be used.

A suitable dosage of the pharmaceutical composition according to the present invention may vary according to the patient's general health and weight, the severity of disease, the form of drug, and the route and period of administration, but may be properly selected by a person skilled in the art. Nonetheless, it is recommended that the composition of the present invention is administered daily at 0.2 mg/kg to 200 mg/kg, preferably 2 mg/kg to 100 mg/kg, to obtain a desirable effect. The administration may be once a day or spread out over multiple times a day. However, said dosage does not, in any way, limit the scope of the present invention.

The pharmaceutical composition according to the present invention may be administered via a variety of routes to mammals, such as rats, mice, livestock, and humans. Any mode of administration may be employed; for example, the administration may be via an oral, rectal or intravenous, intramuscular, subcutaneous, intrauterine, or epidural or intracerebroventricular injection.

The food composition according to the present invention may be widely used in drugs, foods, beverages, etc. for treating and repairing wounds. Foods that may comprise the compound of the present invention include, for example, a variety of foodstuffs, beverages, gums, teas, vitamin complexes, dietary supplements, etc. They may be in the form of powders, granules, tablets, capsules, or drinks.

Concerning the amount of said compound in food or beverages of the present invention, in general, a health food composition according to the present invention may be added 0.01% to 15% by weight of the total food weight; a health beverage composition according to the present invention may be added 0.02 g to 5 g, preferably 0.3 g to 1 g, based on 100 ml.

Besides containing said compound as an essential ingredient at a suggested proportion, the functional beverage composition according to the present invention is not particularly limited in terms of the liquid component and, like common beverages, may contain various sweeteners or natural carbohydrates as an additional ingredient. Examples of said natural carbohydrates are common sugars, including monosaccharides, e.g., glucose, fructose, etc.; disaccharides, e.g., maltose, sucrose, etc.; polysaccharides, e.g., dextrin, cyclodextrin, etc., and sugar alcohols, including xylitol, sorbitol, erythritol, etc. Apart from said sweeteners, natural sweeteners (thaumatin and stevia extracts, e.g., rebaudioside A, glycyrrhizin, etc.) and synthetic sweeteners (saccharin, aspartame, etc.) may be used to an advantage. The proportion of said natural carbohydrates is generally about 1 g to 20 g, preferably about 5 g to 12 g, per 100 ml of the composition of the present invention.

Apart from said ingredients, the composition according to the present invention may contain various nutritional supplements, vitamins, minerals (electrolytes), flavorings including synthetic flavors and natural flavors, colorings and fillers (cheese, chocolate, etc.), pectic acids and their salts, alginic acids and their salts, organic acids, protective colloid thickeners, pH control agents, stabilizers, preservatives, glycerin, alcohols, carbonating agents used for carbonated drinks, etc. In addition, the compositions according to the present invention may contain flesh that is used for preparing natural fruit juices, fruit juice drinks, or vegetable drinks. Such ingredients may be used independently or in combination. Although the proportions of these additives are not of great importance, they are generally selected from the range of 0 to 20 parts by weight per 100 parts by weight of the composition of the present invention.

As described above, the composition according to the present invention, comprising an indirubin derivative for stimulating longitudinal bone growth, has an effect of treating or preventing short stature, microplasia, dwarfism, or precocious puberty. In addition, unlike conventional therapeutic agents for growth, indirubin-3'-oxime regulates the signaling pathway based on specific targets involved in height growth, and therefore, produces a clear effect. Not only that, but indirubin-3'-oxime is a low molecular weight compound that has potential as a therapeutic agent for leukemia. Hence, it has low toxicity, as well as low development cost.

BRIEF DESCRIPTION OF THE DRAWINGS

FIG. 1A and FIG. 1B show the increase in the total length depended on the concentration change. FIG. 1C shows the comparison of cell conditions in the tibia, using safranin staining procedure. And, FIG. 1D shows the dependence of cell conditions on concentration change, which resulted in the increase in the total length (the resting zone-RZ, the proliferating zone-PZ, and the hypertrophic chondrocyte zone-HZ) that depended on the concentration of indirubin-3'-oxime.

FIG. 2A shows indirubin-3'-oxime increased the stability of β-catenin while increasing the amount of inactive GSK3, according to the concentration change. FIG. 2B shows the cell images staining with green color for β-catenin, red color for Col2a1, and blue color for nucleus. And, FIG. 2C shows that the amount of β-catenin markedly increased in the hypertrophic chondrocyte zone of ex vivo tibiae treated with indirubin-3'-oxime.

FIG. 3A shows the experimental schedules (7-week-old mice were treated with indirubin-3'-oxime for 2 weeks, and the amount of activity of the growth plate was compared with that in the control group at 9 weeks). FIG. 3B shows the cell conditions in the growth plate which were observed using the hematoxylin-eosin staining procedure. And, FIG. 3C show the IHC analysis about the indirubin-3'-oxime effect according to FIG. 3A schedule.

FIG. 4A shows the administration time of indirubin-3'-oxime to understand whether indirubin-3'-oxime can actually produce an increase in bone length in mice. FIG. 4B shows that the effect on the activity of the growth plate in the middle of a period of growth was examined using the hematoxylin-eosin staining procedure. FIG. 4C shows that Indirubin-3'-oxime treatment increases not only the length of each zone but also the total length of the growth plate. FIG. 4D shows that Indirubin-3'-oxime treatment ultimately leads to an increase in the total bone length of the tibia. And, FIG. 4E shows the above described effect of Indirubin-3'-oxime treatment lasts even in 13-week-old mice in which height growth completely ceased.

DETAILED DESCRIPTION

Figure 1A:
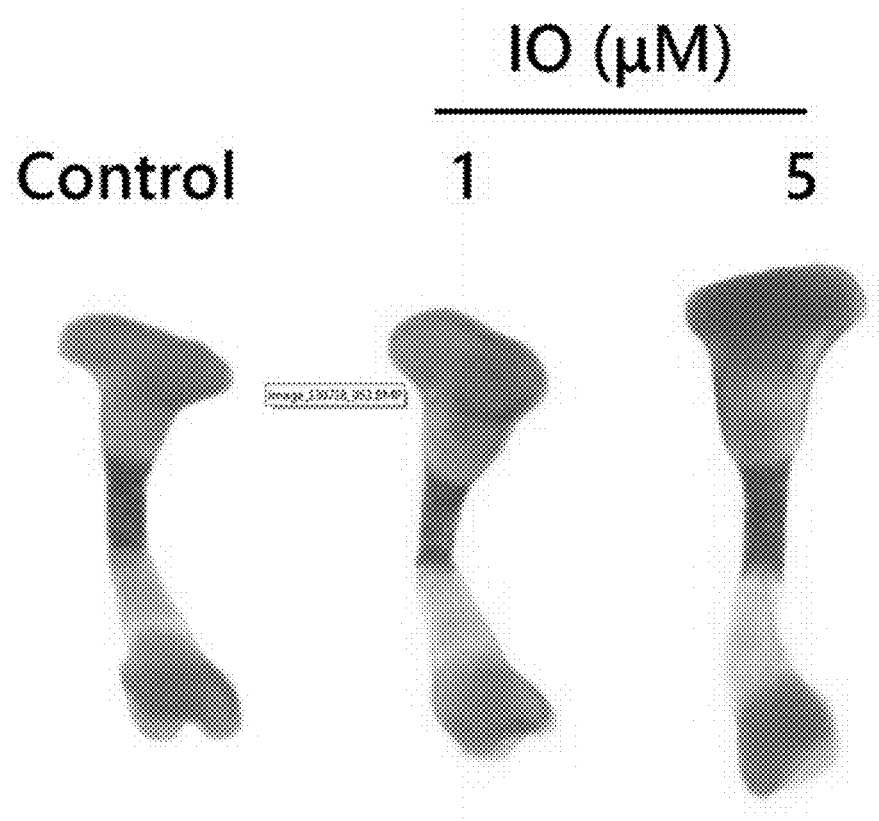
FIGS. 1A-1D illustrate that indirubin-3'-oxime dose-dependently induces longitudinal bone growth of ex vivo tibia. More specifically.

Hereinafter, the present invention is described in detail through the following examples. However, these examples are only intended to illustrate the present invention and do not limit the scope of the invention.

Example 1: Cell Culture and Reagents

Rat chondrosarcoma (RCS) cells were cultured in a Dulbecco's modified Eagle's medium (DMEM; Gibco, Grand Island, N.Y.), supplemented with 10% fetal bovine serum (FBS) and penicillin/streptomycin.

Example 2: Western Blot Analysis

For Western blot analysis, cells were treated with indirubin-3'-oxime for 24 hours, cultured and reached to 70% confluency and then were harvested. After the harvested samples underwent cytolysis, the proteins were quantified, which was followed by electrophoresis using 10% or 12% SDA-PAGE gel. Afterwards, immunoblot was conducted using antibodies.

Example 3: Immunocytochemistry $2.5 \times 10^4$ cells were adhered to a cover glass placed in a 12-well plate. Once securely attached, cells were treated with indirubin-3'-oxime for 24 hours, and then were rinsed with a phosphoric acid buffer solution. After adding 4% paraformaldehyde, cells were fixed at room temperature for 20 min. Then, proteins expressed in the cells were observed through cell membrane permeation, blocking, and immunofluorescent staining processes.

Example 4: Tissue Culture and Reagents

The tibiae were separated from 15.5-embryonic-day-old C57BL/6 mice, and were incubated in a 24-well tissue culture dish for 7 days. The medium used was prepared by adding 10% FBS, 1 mM beta-polyglycerol disodium phosphate, 50 ng/ml ascorbic acid, 0.3 mg/ml L-glutamine, 0.2% BSA, 100 U/ml penicillin, and 100 μg/ml streptomycin to a minimal essential medium (α-MEM, Gibco). Then, the tibiae were separated from the mice. After being treated in the medium for 24 hours, the tibia was treated with a drug. The medium and the drug were changed every two days. The tibia length was measured before and after treatment with the drug. The tibial tissue, on which drug treatment was completed, was rinsed with PBS and then fixed using 4% formaldehyde.

Example 5: Mouse Model

Two and six-week-old C57BL/6 mice, purchased from KOATECH (Gyeonggi-do, South Korea), were cared for in accordance with the guidelines established by the Institutional Animal Care and Use Committee at Yonsei University. The mice were divided into a control group and an experimental group, and were adapted to the environment for 1 week. Afterwards, they were treated every day for 2 weeks with a solution containing 20% dimethyl sulfide and 30% ethanol, or with indirubin-3'-oxime (0.05 mg/kg, 0.1 mg/kg, and 0.5 mg/kg), via intraperitoneal injection. Two weeks later, the tibiae were separated from mice, and then the muscles were separated and removed, after which the bones were fixed using 4% formaldehyde. The bones were treated for 2 weeks with a 10% EDTA solution for the decalcification process. The EDTA solution was changed every two days.

Example 6: Staining of the Tibia

The tissue-cultured embryo tibiae and the animal-tested tibiae were dewaxed in xylene, and were rehydrated in a stepwise-diluted ethanol solution. The tibial tissue, which was separated from 15.5-embryonic-day-old ICR mice and then tissue-cultured, was stained using the safranin staining procedure. Staining was carried out for 25 min in a 0.02% fast green solution, and after brief dipping in acetic acid, was again carried out for 7 min in a 0.1% safranin solution. Meanwhile, the tibial tissue that was animal-tested and decalcified in EDTA was stained via the hematoxylin-eosin staining procedure. The tissue was stained in a hematoxylin solution for 10 min and then rinsed in running water for 10 min. After being briefly dipped in a solution comprising 0.1% hydrochloric acid and 70% ethanol, the tissue was stained for 30 sec in an eosin solution. The stained tibial tissues again underwent a dehydration process in the stepwise-diluted ethanol solution and were dewaxed in xylene.

Example 7: Immunohistochemistry

The tibiae that underwent a dewaxing process were dehydrated. After paraffin blocks were formed, the tissues were sectioned at 4-μm thickness. The sectioned tissues were rehydrated, and then stained using immunofluorescence.

Increase in the Length of the Tibia Due to indirubin-3'-oxime

Figure 1B:
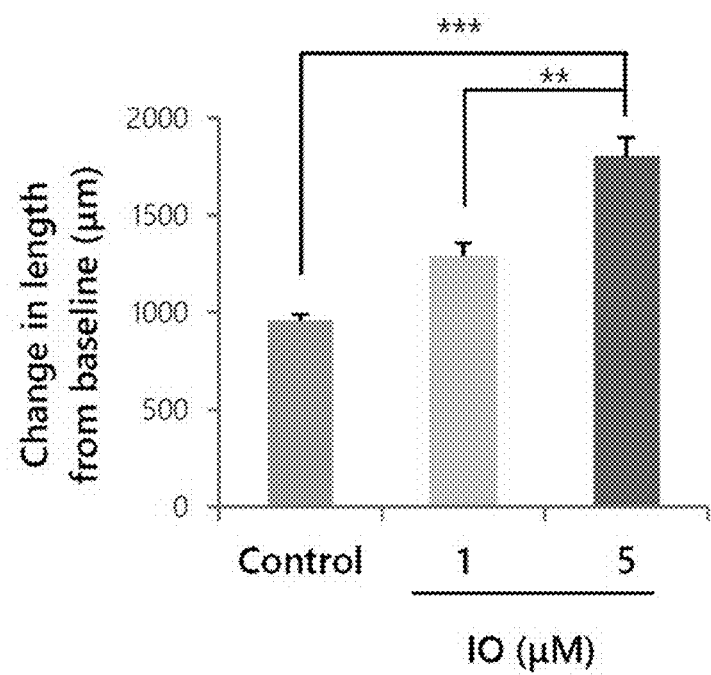
Figure 1C:
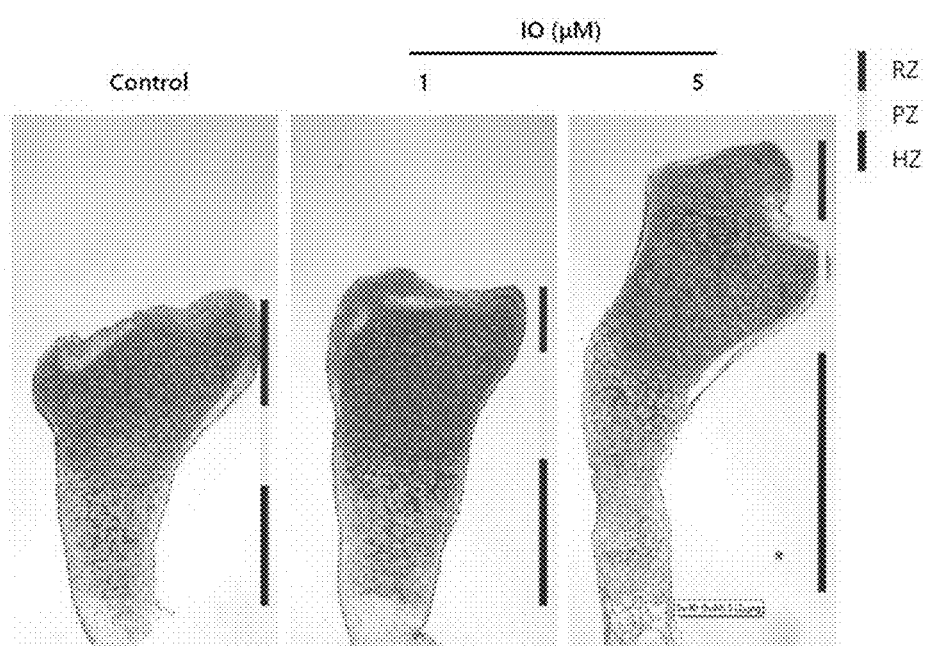
Figure 1D:
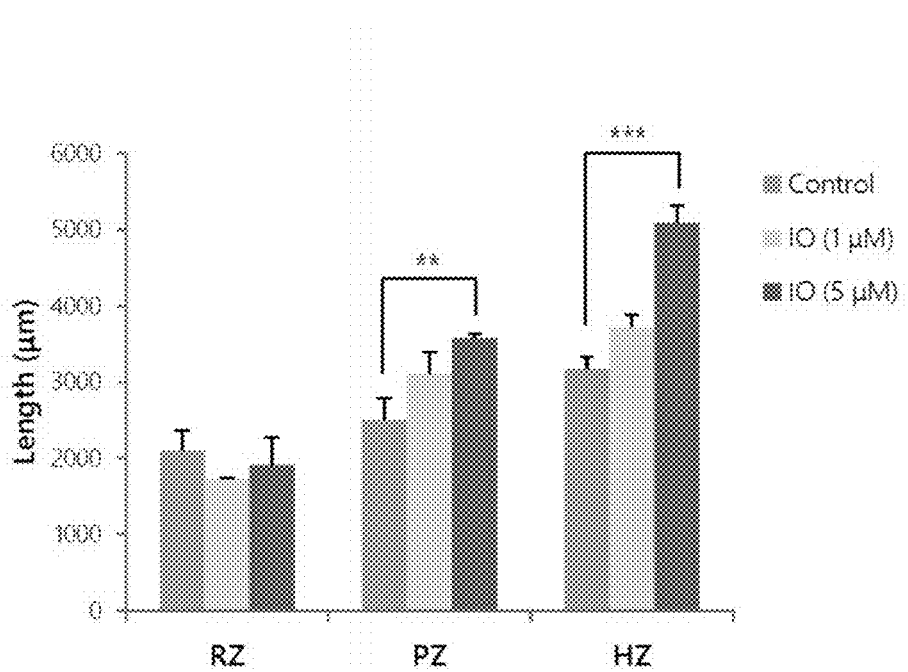

To obtain a more accurate understanding of the effect of indirubin-3'-oxime on ex vivo tibia culture, two different concentrations (1 μM and 5 μM) of indirubin-3'-oxime were treated to tibiae for 6 days. The results show that the increase in the total length depended on the concentration change (FIGS. 1A and 1B). Moreover, the comparison of cell conditions in the tibia, using the safranin staining procedure (FIG. 1C), shows the dependence of cell conditions on concentration change, which resulted in the increase in the total length (the resting zone, the proliferating zone, and the hypertrophic chondrocyte zone) that depended on the concentration of indirubin-3'-oxime (FIG. 1D).

Increase in the Stability of β-Catenin Due to indirubin-3'-oxime

Figure 2A:
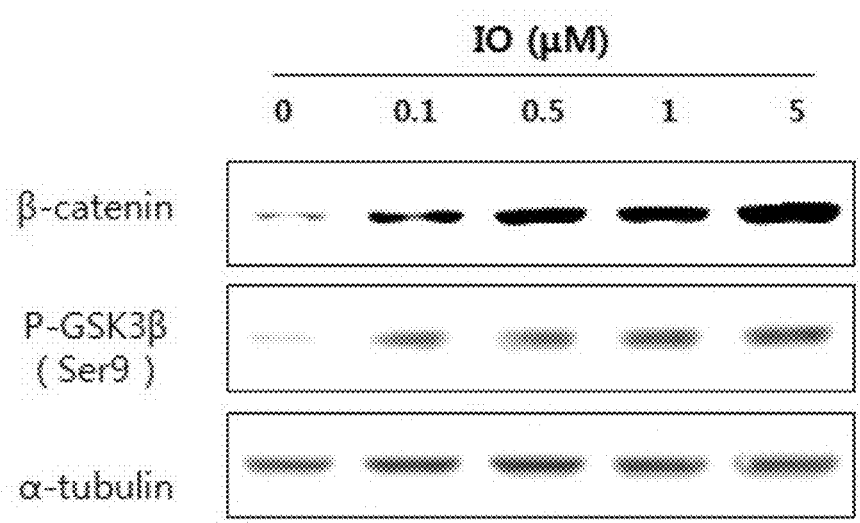
FIGS. 2A-2C illustrate that indirubin-3'-oxime enhances chondrocyte maturation via the Wnt/β-catenin pathway. More specifically.
Figure 2B:
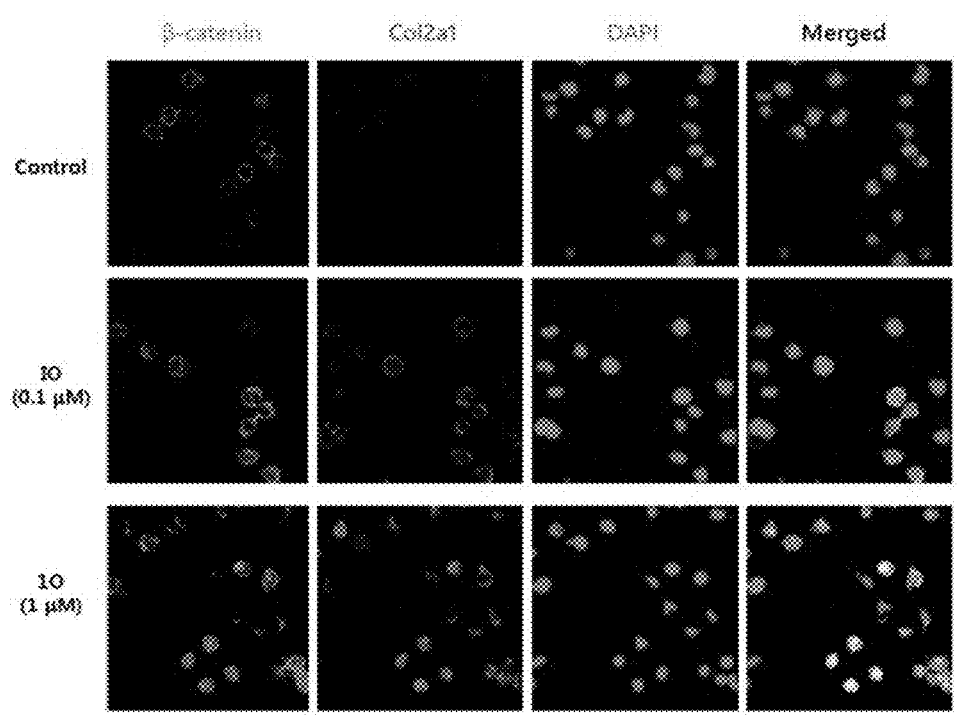
Figure 2C:
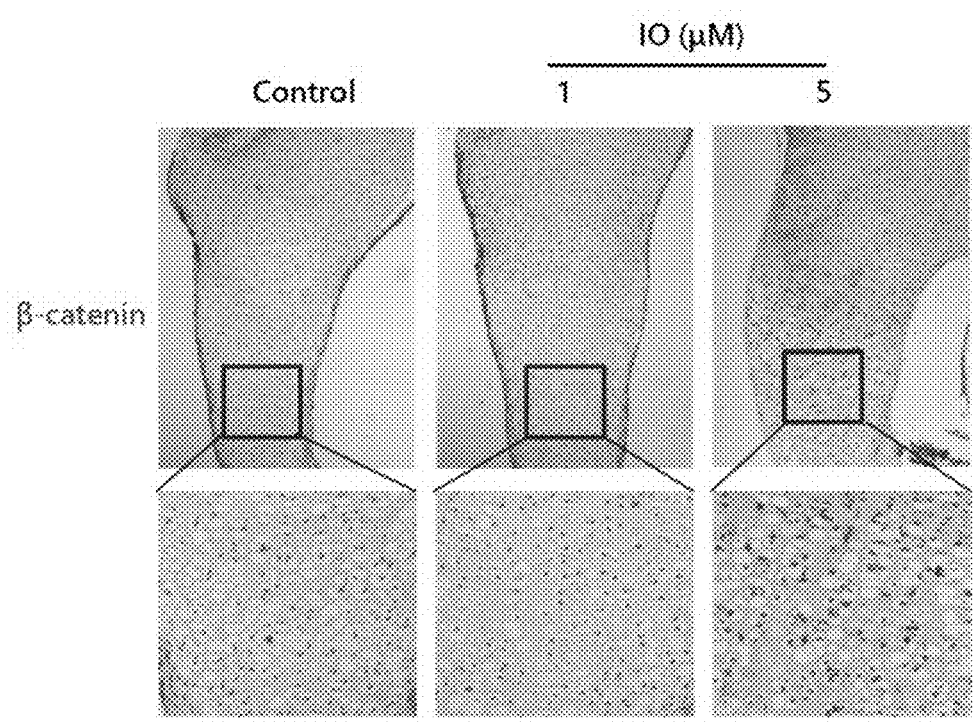

Indirubin-3'-oxime, a GSKβ inhibitor, is already known to increase the stability of β-catenin. To test whether such an effect is actually produced in chondrocytes, the present inventors conducted Western blot using RCS cells, and found that indirubin-3'-oxime increased the stability of β-catenin while increasing the amount of inactive GSKβ, according to the concentration change (FIG. 2A). ICC analysis confirmed that this increase in the stability of β-catenin resulted from an increase in the amount of β-catenin that was translocated into the nucleus. In addition, IHC analysis on ex vivo tissues showed that the amount of β-catenin markedly increased in the hypertrophic chondrocyte zone of ex vivo tibiae treated with indirubin-3'-oxime.

Figure 3A:
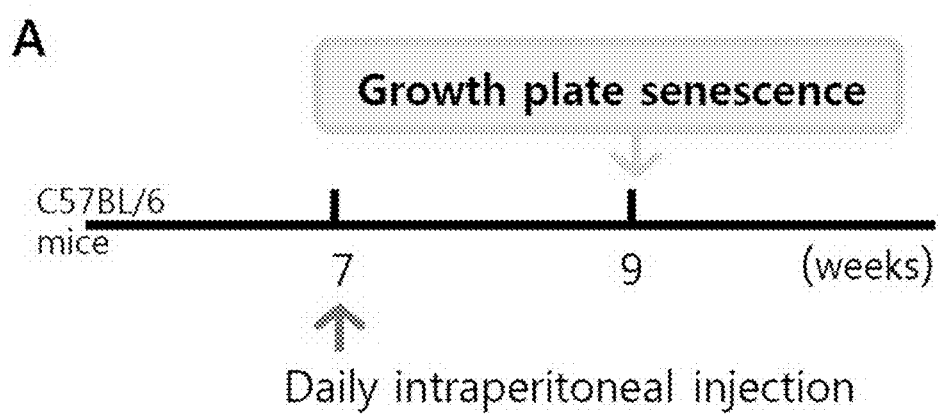
FIGS. 3A-3C illustrate that indirubin-3'-oxime inhibits growth plate senescence. More specifically.
Figure 3B:
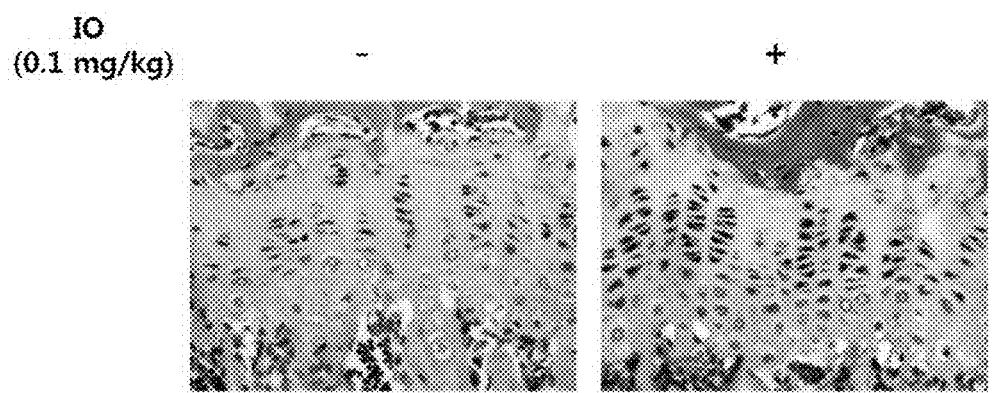
Figure 3C:
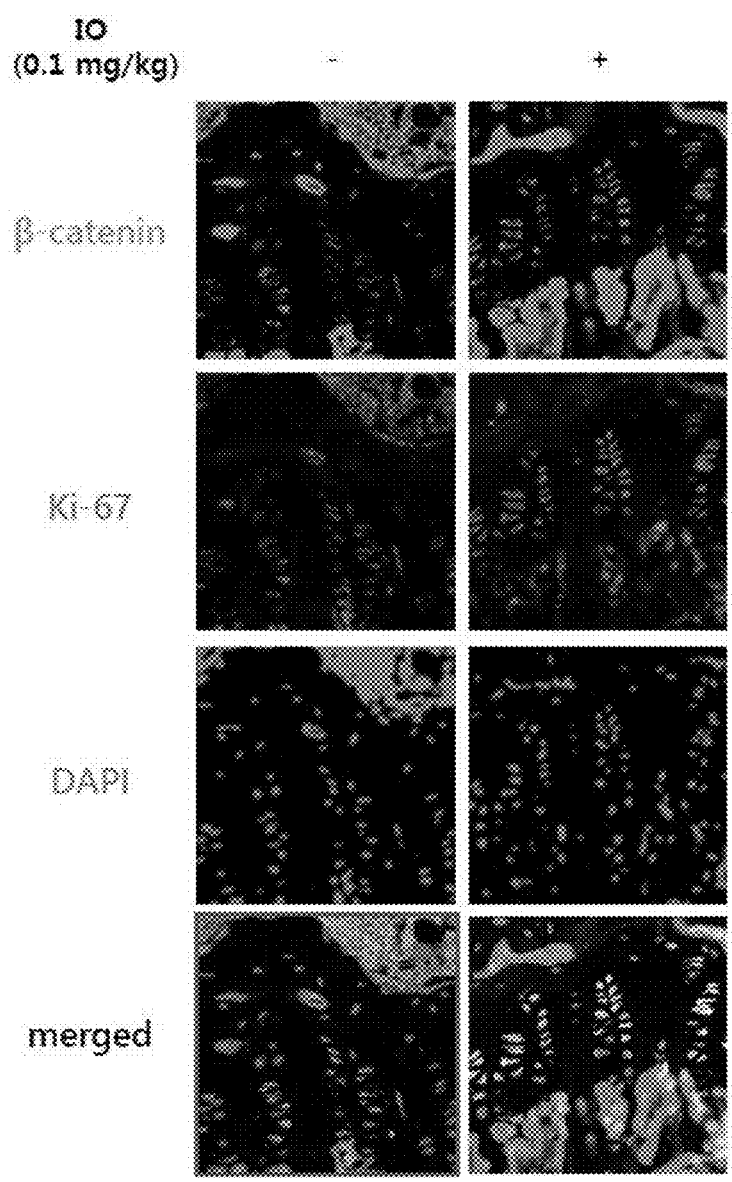

Increase in the Activity of the Growth Plate in Mice Dosed with indirubin-3'-oxime As humans reach adulthood, the growth plate is reduced in size and eventually closes, thus preventing further height growth. In mice, growth plates do not close. However, there is a marked decline in the activity of cells inside the growth plate from 8 weeks of age, and height growth gradually comes to a halt. In the present experiment, the effect of indirubin-3'-oxime on the activity of the growth plate was investigated. 7-week-old mice were treated with indirubin-3'-oxime for 2 weeks, and the amount of activity of the growth plate was compared with that in the control group at 9 weeks (FIG. 3A). Cell conditions in the growth plate were observed using the hematoxylin-eosin staining procedure. As a result, the activity of the growth plate was still maintained in 9-week-old mice under treatment with indirubin-3'-oxime (FIG. 3B). This effect of indirubin-3'-oxime was identified through IHC analysis to be an increase in the amount of Ki67, a marker related to cell proliferation, along with an increase in the stability of β-catenin. These results suggest the possibility of indirubin-3'-oxime as an agent for growth that can delay the time point at which the growth plate closes in humans.

Increase in the Length of the Tibia in Mice Dosed with indirubin-3'-oxime

Figure 4A:
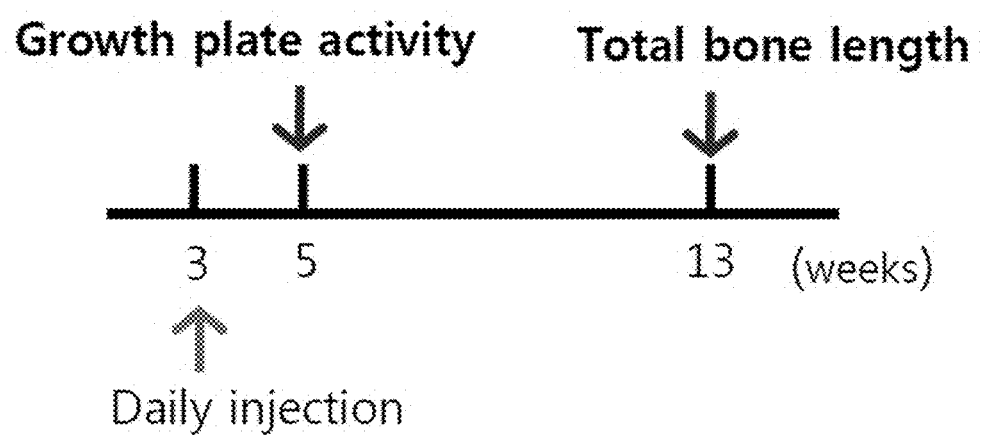
FIGS. 4A-4E illustrate that indirubin-3'-oxime promotes longitudinal bone growth. More specifically.
Figure 4B:
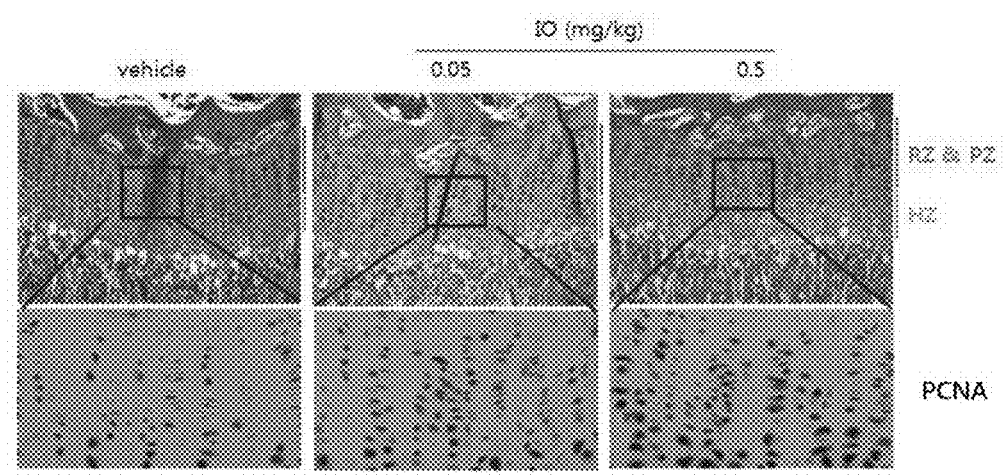
Figure 4C:
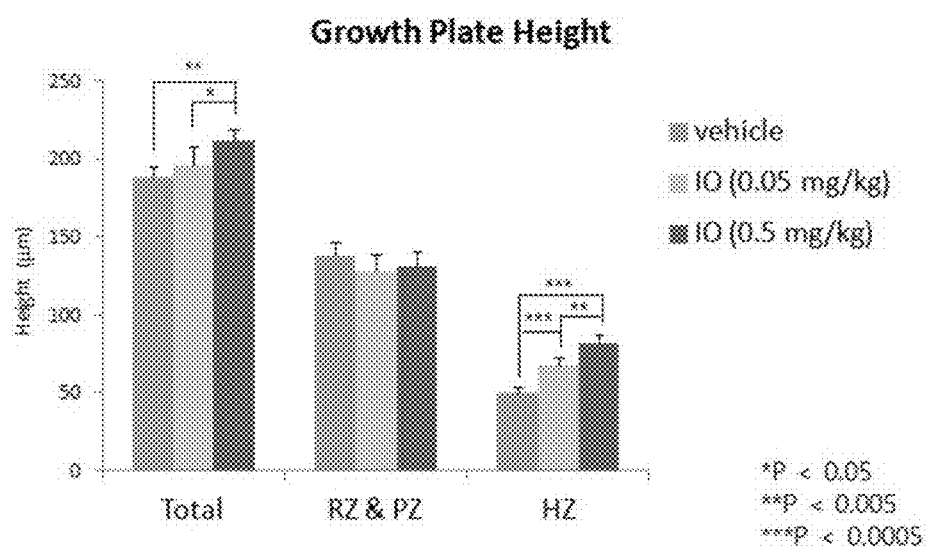
Figure 4D:
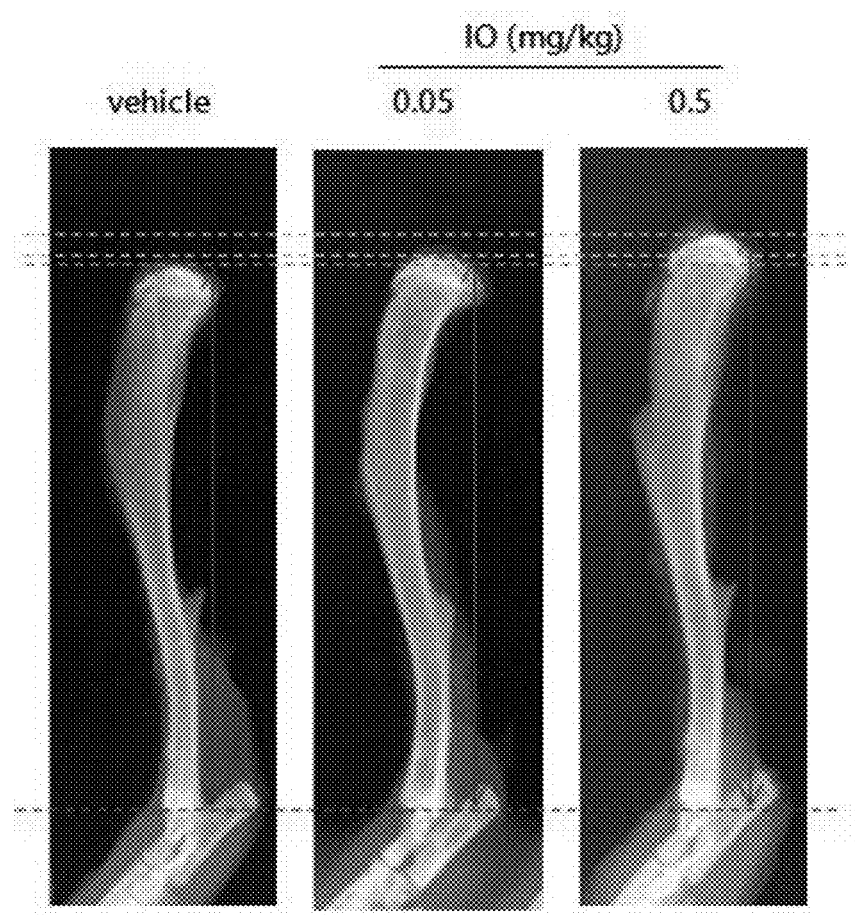
Figure 4E:
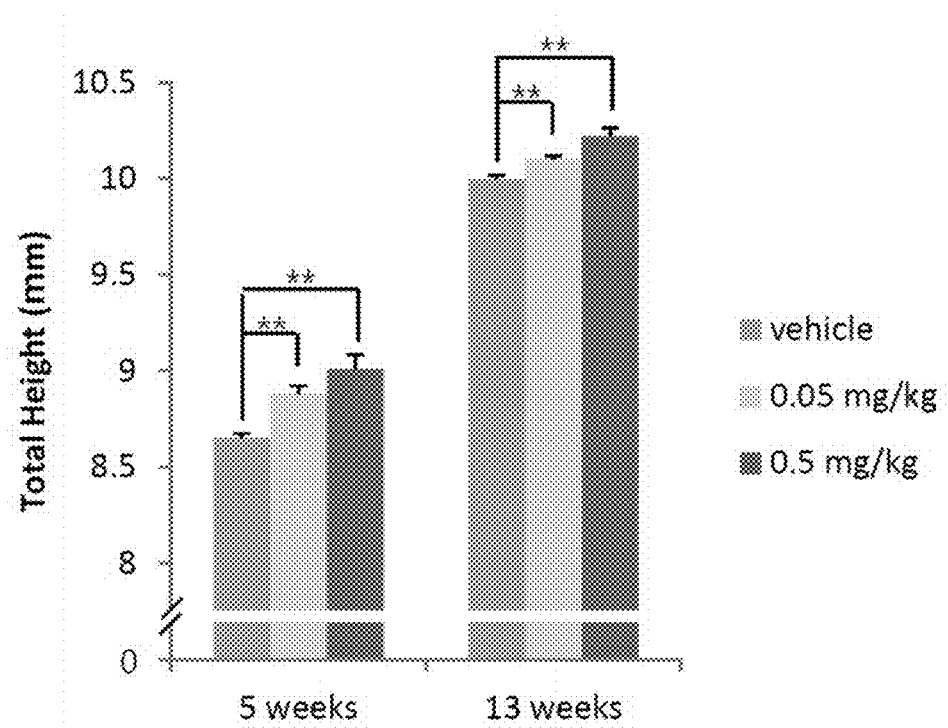

To understand whether indirubin-3'-oxime can actually produce an increase in bone length in mice, indirubin-3'-oxime was administered during a period of active growth, and its effect was examined (FIG. 4A). First of all, the effect on the activity of the growth plate in the middle of a period of growth was examined using the hematoxylin-eosin staining procedure (FIG. 4B). Indirubin-3'-oxime treatment was found to result in an increase not only in the length of each zone but also in the total length of the growth plate (FIG. 4C). Cell proliferation markers related to these effects were once again confirmed through PCNA (FIG. 4B). Moreover, these results ultimately led to an increase in the total bone length of the tibia. In addition, these effects were found to last even in 13-week-old mice, in which height growth completely ceased (FIGS. 4D, 4E).

In conclusion, the above results suggest that indirubin-3'-oxime effectively increases longitudinal bone length by activating the Wnt/β-catenin signaling pathway via inhibition of GSK-3β. Furthermore, because of its ability to delay the time point at which the growth plate closes, indirubin-3'-oxime proves to be an effective therapeutic agent that may overcome the current problem of early closure of the growth plate resulting from precocious puberty.

So far, the present invention was described with reference to the examples. However, a person skilled in the art could understand that various changes can be made without exceeding the scope of the present invention, and that the elements can be replaced with their equivalents. Moreover, from the numerous changes made without exceeding the essential scope of the present invention, specific aspects and materials can be employed within the teachings of the present invention. Thus, the present invention should be construed not to be limited in terms of the specific examples disclosed as the best modes contemplated for carrying out the present invention, but to include all examples that fall under the scope of the claims attached hereto.

The invention claimed is:

1. A method of treating an animal having longitudinal bone growth disorders comprising administering an effective amount of compound indirubin-3'-oxime to the animal.

2. The method of claim 1, wherein the administering an effective amount of compound indirubin-3'-oxime to the animal such that a length of the tibia increase.

3. The method of claim 1, wherein the administering an effective amount of compound indirubin-3'-oxime to the animal such that an activity of the growth plate increase.

4. The method of claim 1, wherein the longitudinal bone growth disorder is short stature, microplasia, dwarfism, or precocious puberty.

\* \* \* \* \*